US009454682B2

(12) United States Patent
Tiedemann

(10) Patent No.: US 9,454,682 B2
(45) Date of Patent: Sep. 27, 2016

(54) NEAR FIELD COMMUNICATION READER DEVICE, NEAR FIELD COMMUNICATION TAG DEVICE, NEAR FIELD COMMUNICATION SYSTEM AND NEAR FIELD COMMUNICATION METHOD

(75) Inventor: Stephen Tiedemann, Stuttgart (DE)

(73) Assignee: SONY Corporation, Tokyo (JP)

(*) Notice: Subject to any disclaimer, the term of this patent is extended or adjusted under 35 U.S.C. 154(b) by 20 days.

(21) Appl. No.: 13/614,833

(22) Filed: Sep. 13, 2012

(65) Prior Publication Data
US 2013/0241709 A1   Sep. 19, 2013

(30) Foreign Application Priority Data
Sep. 20, 2011  (EP) .................................... 11007654

(51) Int. Cl.
G06K 7/10   (2006.01)
H04L 1/00   (2006.01)
H04B 5/00   (2006.01)
H04W 4/00   (2009.01)
A61B 5/00   (2006.01)

(52) U.S. Cl.
CPC ......... G06K 7/10237 (2013.01); H04B 5/0031 (2013.01); H04B 5/0056 (2013.01); H04L 1/0079 (2013.01); H04W 4/008 (2013.01); A61B 5/0015 (2013.01); H04M 2250/04 (2013.01)

(58) Field of Classification Search
CPC ........ H04Q 5/22; G08B 13/14; H04W 76/02
USPC ............................... 340/10.2, 10.1
See application file for complete search history.

(56) References Cited

U.S. PATENT DOCUMENTS

| 2004/0103285 | A1* | 5/2004 | Nishitani et al. ............. 713/176 |
| 2005/0285742 | A1* | 12/2005 | Charych et al. ........... 340/572.1 |
| 2006/0074889 | A1* | 4/2006 | Andrews et al. ................ 707/3 |
| 2007/0075834 | A1* | 4/2007 | Armstrong et al. ......... 340/10.1 |
| 2008/0162312 | A1 | 7/2008 | Sklovsky et al. |
| 2009/0045913 | A1* | 2/2009 | Nelson et al. ............... 340/5.66 |
| 2009/0070336 | A1* | 3/2009 | Wiechers et al. .............. 707/10 |
| 2009/0102682 | A1* | 4/2009 | Corndorf ................ 340/870.31 |

(Continued)

OTHER PUBLICATIONS

Search Report issued Feb. 6, 2015, in European Patent Application No. 12006044.7.
"Health informatics—Personal health device communication, Part 20601: Application profile—Optimized Exchange Protocol" IEEE Engineering in Medicine and Biology Society, IEEE Std 11073-20601, XP017604162, Dec. 19, 2008.

(Continued)

Primary Examiner — Jennifer Mehmood
Assistant Examiner — Pameshanand Mahase
(74) Attorney, Agent, or Firm — Oblon, McClelland, Maier & Neustadt, L.L.P.

(57) ABSTRACT

A near field communication reader device is provided including a transmitter to transmit a request to a near field communication tag device; wherein the request is formed according to a predetermined format including an identifier section for carrying a request identifier; a receiver to receive a response from the near field communication tag device; wherein the response is formed based on the request according to the predetermined format including the identifier section for carrying a response identifier; and a processor to generate the request identifier, to compare the request identifier with the response identifier and to accept the response as a valid response if the response identifier is different from the request identifier. A corresponding near field communication tag device, a near field communication system and a near field communication method are provided as well.

15 Claims, 6 Drawing Sheets

(56) References Cited

U.S. PATENT DOCUMENTS

| | | |
|---|---|---|
| 2009/0248437 A1 | 10/2009 | Gucciardi et al. |
| 2010/0045425 A1 | 2/2010 | Chivallier |
| 2010/0299527 A1 | 11/2010 | Arunan et al. |
| 2011/0143661 A1 | 6/2011 | Hartwig et al. |
| 2012/0179737 A1* | 7/2012 | Baranov ............ H04W 76/023 709/201 |

OTHER PUBLICATIONS

"Android NDEF Push Protocol Specification", Version 1, XP055163343, Feb. 22, 2011.

"Simple NDEF Exchange Protocol, Technical Specification, SNEP 1.0", XP055081363, Aug. 31, 2011.

* cited by examiner

NEAR FIELD COMMUNICATION READER DEVICE, NEAR FIELD COMMUNICATION TAG DEVICE, NEAR FIELD COMMUNICATION SYSTEM AND NEAR FIELD COMMUNICATION METHOD

CROSS REFERENCE TO RELATED APPLICATION

The present application claims the benefit of the earlier filing date of 11 007 654.4 filed in the European Patent Office on Sep. 20, 2011, the entire content of which application is incorporated herein by reference.

The invention relates to a near field communication reader device, to a near field communication tag device, to a near field communication system and to a near field communication method.

BACKGROUND

Personal health devices compliant with ISO/IEEE 11073 standards can communicate with each other using ISO/IEEE 11073-20601 communication protocol. ISO/IEEE 11073-20601 standard defines two entities, called "agent" and "manager". An agent is a node that collects and transmits personal health data to an associated manager. The manager is a node that receives data from one or more agents. Examples of managers include a cellular phone, health monitor gateway, set top box of computer system. ISO/IEEE 11073-20601 standard defines the data formats from the various health care parameters and the communication protocol used between ISO 11073-20601 agent and ISO 11073-20601 manager.

As part of the ISO/IEEE 11073 family of standards for medical and health device communication, the ISO/IEEE 11073-20601 optimized exchange protocol defines a common framework for making an abstract model of personal health data available in transport-independent transfer syntax. The transfer syntax includes the methods required to establish logical connections between devices and to provide presentation capabilities and services needed to perform communication tasks. The protocol is optimized to personal health usage requirements.

Near field communication, or NFC, allows for simplified transactions, data exchange, and wireless connections between two devices in close proximity to each other, usually by no more than a few centimeters. The Near Field Communication Forum (NFC Forum) formed in 2004 promotes sharing, pairing, and transactions between NFC devices and develops and certifies device compliance with NFC standards.

Health data is exchanged as IEEE 11073-20601 optimized exchange protocol application protocol data units (APDUs) encapsulated in Near field communication (NFC) Forum data exchange format (NDEF) records.

To facilitate communication, a manager (NFC reader device) must constantly test if new NDEF data is available from an agent (NFC tag device).

It is object of the invention to facilitate the test for new data from the NFC tag device.

The object is solved by a near field communication reader device, a near field communication tag device, a near field communication system and a near field communication method according to claims 1, 5, 9 and 10, respectively. Details of the invention will become more apparent from the following description of embodiments in the connection with the accompanying drawings.

DETAILED DESCRIPTION OF THE INVENTION

In the following embodiments of the invention are described. It is important to note that all described embodiments in the following may be combined in any way, i.e. there is no limitation that certain described embodiments may not be combined with others.

Figure 1:
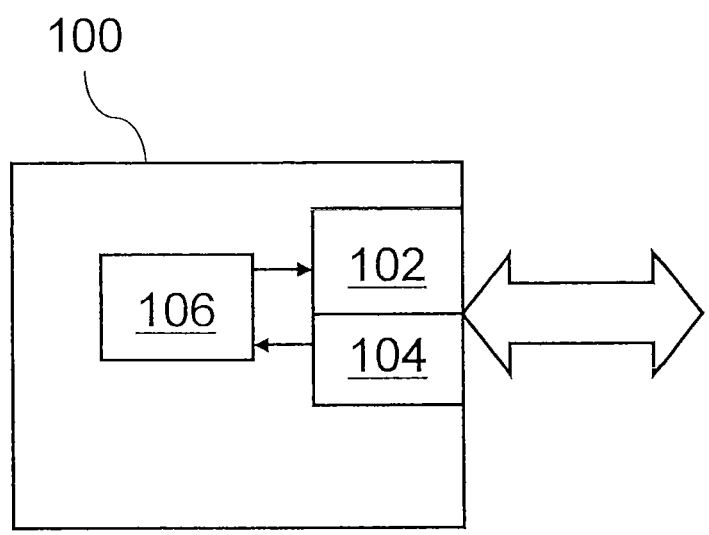
FIG. 1 is a schematic block diagram of a near field communication reader device according to an embodiment of the invention.

In FIG. 1 there is depicted a schematic block diagram of a near field communication reader device 100. The near field communication reader device 100 includes a transmitter 102 adapted to transmit a request to a near field communication tag device (not depicted) wherein the request is formed according to a predetermined format including an identifier section for carrying a request identifier.

The predetermined format might be realized as a near field communication data exchange format (NDEF) (which is explained with regard to FIG. 6 later). However, other predetermined formats including an identifier section might be used as well.

A near field communication tag device transfers data by modulating radio waves transmitted from the near field communication reader. A tag can be used as a memory for storing or reading data, or can be connected to a processor in order to exchange data between the reader and the processor.

The near field communication reader device 100 further includes a receiver 104 adapted to receive a response from the near field communication tag device wherein the response is formed according to the predetermined format including the identifier section for carrying a response identifier.

Further a processor 106 is included, wherein the processor is adapted to generate the request identifier, and to compare the request identifier with the response identifier and to accept the response as a valid response if the response identifier is different from the request identifier.

In certain embodiments, a valid response might only be accepted if the response is received within a predetermined time interval after transmitting the request.

The near field communication reader device might be referred to also as NFC reader device, as NFC Forum device in reader/writer mode or as NFC Forum reader device. The near field communication tag device might also be referred to as NFC tag device or as NFC Forum tag. Near field communication between an NFC reader device and an NFC tag device is implemented by allowing the NFC reader device to read or write data from or to the NFC tag device. The NFC tag device may only transmit data to the NFC reader device in response to a read operation from the NFC reader device.

Figure 2:
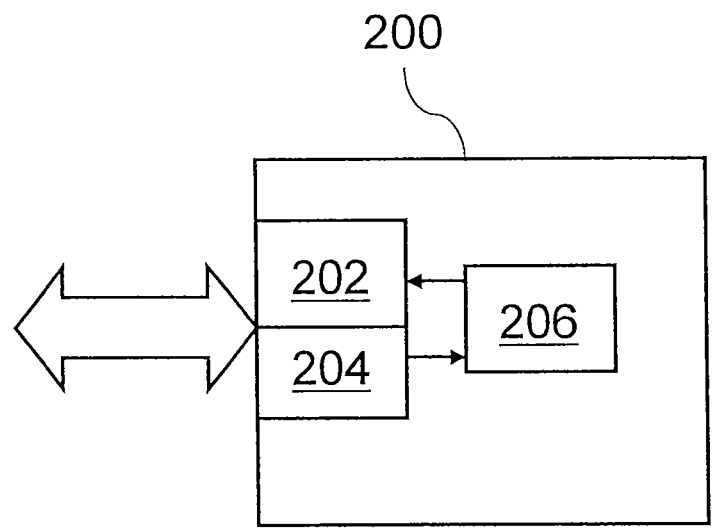
FIG. 2 is a schematic block diagram of a near field communication tag device according to an embodiment of the invention.

In FIG. 2 a schematic block diagram of a near field communication tag device 200 is depicted. The near field communication tag device 200 includes a tag receiver 204 to receive a request from a near field communication reader device 100 (not depicted) wherein the request is formed according to predetermined format including an identifier section for carrying a request identifier. Further, a tag transmitter 202 is included, the tag transmitter 202 being adapted to transmit a response to the near field communication reader device 100, wherein the response is formed according to the predetermined format including the identifier section for carrying a response identifier. Further, the near field communication tag device 200 includes a tag processor 206 adapted to read the request from the tag receiver 202, to generate a response based on the request and to forward the response to the tag transmitter 204, wherein the response identifier is different from the request identifier.

The IEEE 11073-20601 protocol requires that an IEEE agent is able to send an APDU without a precedent request from the IEEE manager. This can be facilitated by a mechanism where the NFC reader device periodically attempts to read new data from the NFC tag device (poll for data). In such system, the NFC reader device typically first reads an NDEF message from the NFC tag device and subsequently writes an NDEF message to the NFC tag device; this process would repeat until the end of the conversation.

The near field communication reader device 100 and the near field communication tag device 200 according to an embodiment of the invention allows the near field communication reader device 100 to determine if the NDEF message being read represents an actual and expected answer from the near field communication tag device in response to the previously written NDEF message.

Figure 3:
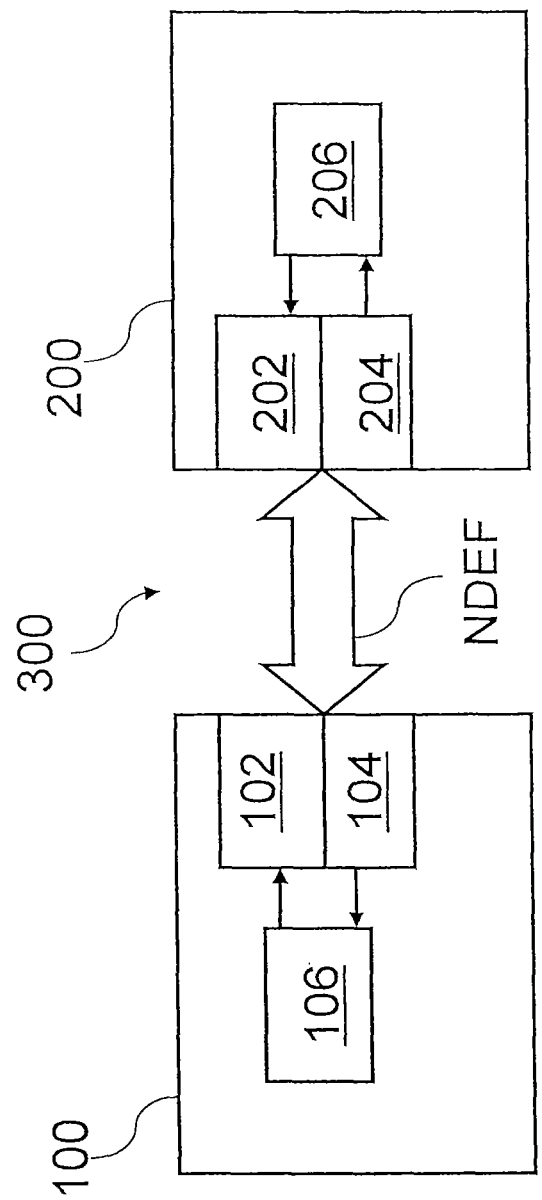
FIG. 3 is a schematic block diagram of a near field communication system according to an embodiment of the invention.

In FIG. 3 a schematic block diagram of a near field communication system 300 is depicted. The near field communication system 300 includes a near field communication reader device 100 and a near field communication tag device 200 exchanging NDEF messages as explained in FIGS. 1 and 2 above.

Figure 4:
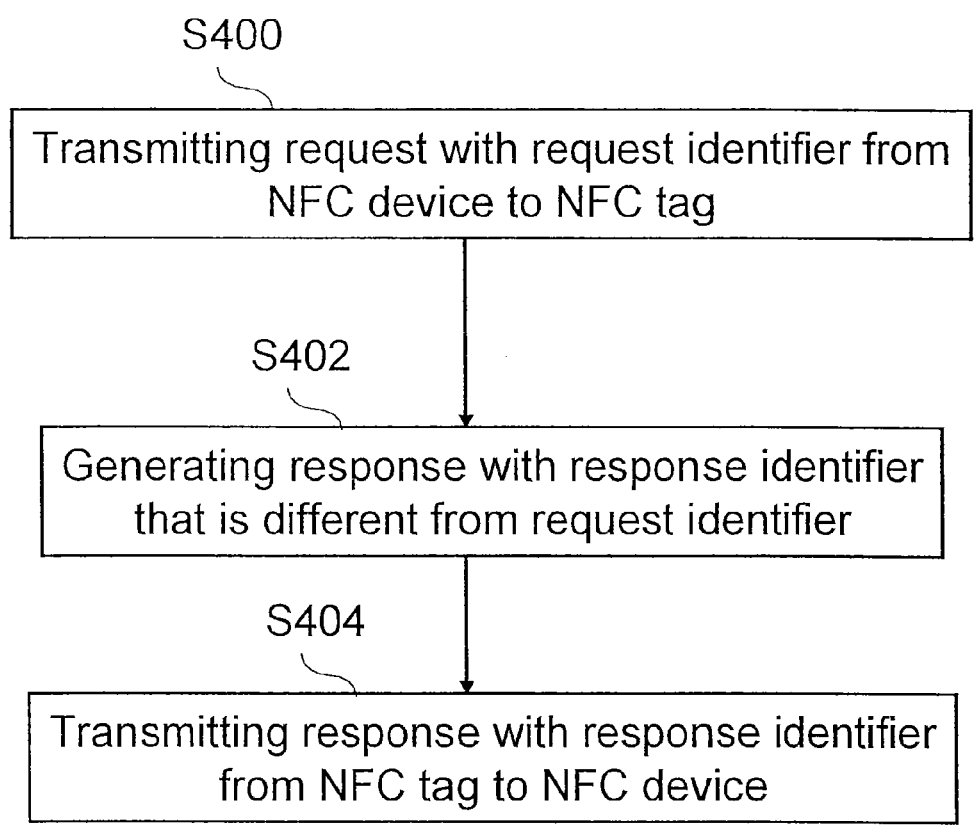
FIG. 4 is a schematic flow diagram of a near field communication method according to an embodiment of the invention.

In FIG. 4 the schematic flow diagram of the near field communication method according to an embodiment of the invention is depicted. In a step S400, the request from a near field communication reader device to a near field communication tag device is transmitted, wherein the request is formed according to a predetermined format including an identifier section for carrying a request identifier.

In a step S402, a response is generated, wherein the response is formed based on the request and according to the predetermined format including the identifier section for carrying a response identifier and the response identifier is different from the request identifier.

In step S404, the response is transmitted from the near field communication tag device 200 to the near field communication reader device 100.

Figure 5:
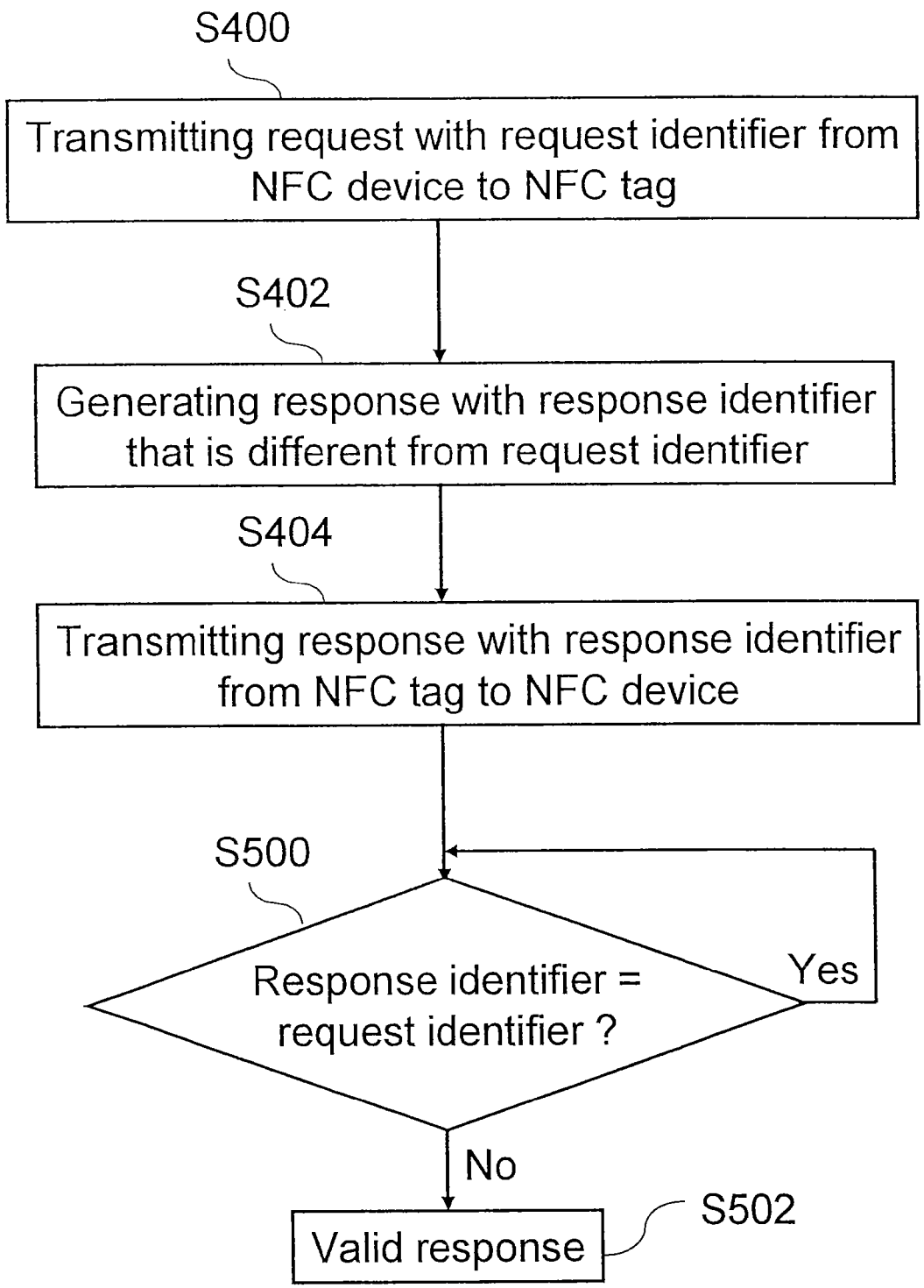
FIG. 5 is a schematic flow diagram of a further method according to an embodiment of the invention.

According to the method depicted in FIG. 5, in a step S500 it is verified, whether the response identifier is different from the request identifier. If the request identifier is different from the response identifier, the response is considered as a valid response S502. If the response identifier is identical to the request identifier the NFC device further listens to the NFC tag until the valid response 502 is received.

Figure 6:
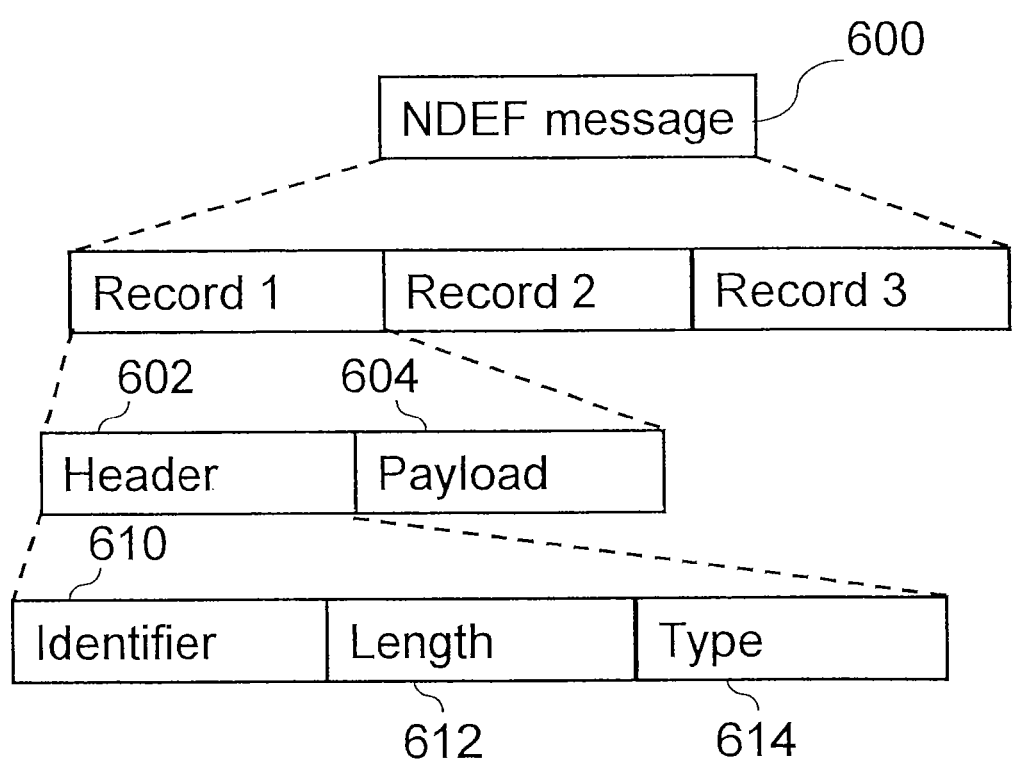
FIG. 6 is a schematic block diagram of a format of an NDEF message.

In FIG. 6 a schematic format for an NDEF message 600 is depicted. The NDEF message 600 includes a plurality of records, in FIG. 6 exemplarily three records, i.e. record 1, record 2 and record 3 are depicted. However, further records are possible. NDEF is a binary message format designed to encapsulate one or more application-defined payloads into a single message construct. An NDEF message contains one or more NDEF records, each carrying a payload 604 of arbitrary type and up to $2^{32}-1$ octets in size. The header 602 includes an identifier section 610, a length section 612 and a type section 614.

According to the embodiments of the invention the response/request identifier is transmitted in the identifier section 610 with every NDEF message being exchanged. In its simplest form, the response/request identifier may represent a message counter that is monotonically increased with every message sent back and forth. This might be realized by adapting the processor 106 of the near field communication reader device 100 and/or the tag processor 206 of the near field communication reader device 200 so that the corresponding request identifiers and/or response identifiers are generated by adding one to the previously received response identifier and/or to add one to the previously received request identifier. Other methods for generating different identifiers are possible as well, such as using a random number generating scheme.

In further embodiments, it might be envisaged to generate the request identifiers and/or the response identifiers by adding two to the previously request identifier and/or response identifier, respectively.

A further possibility might be to generate a request identifier and/or a response identifier by calculating a hash value (fingerprint) of payload data that is transmitted in the payload section 604. Determining the hash value (fingerprint) also results with a sufficient amount of certainty in different values for the response and/or request identifier.

When the message identifier is transmitted as the NDEF identifier (ID) field, the identifier is decoupled from the actual message content in the payload section 604. The embodiments of the invention allow a near field communication reader device that is exchanging data with a near field communication tag device in the form of NDEF messages to determine if the data being read represents an actual response from the near field communication tag device without that information being intermixed with the actual payload or message content.

Figure 7:
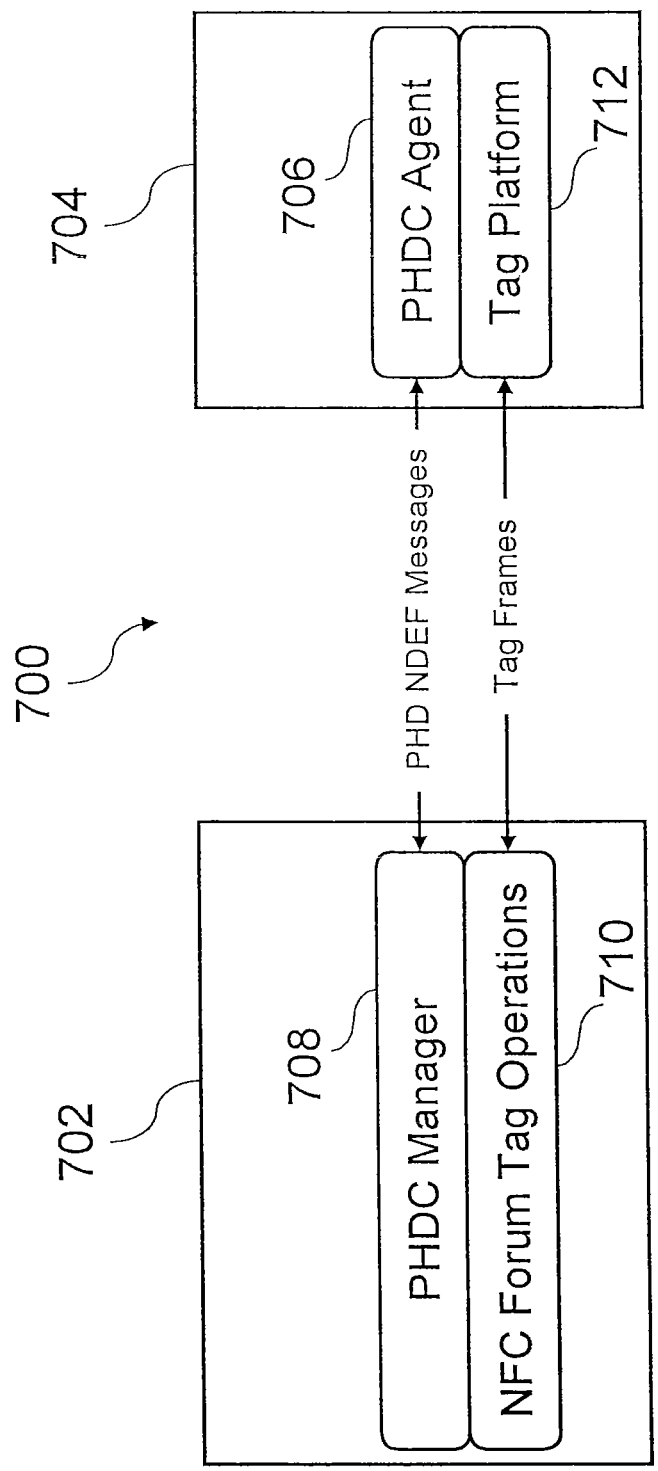
FIG. 7 is a schematic block diagram of a near field communication system according to an embodiment of the invention.

In FIG. 7 a further embodiment of a near field communication system 700 in a reader/writer mode according to the invention is depicted.

An NFC tag device 704 including a PHDC agent 706 exchanges PHD NDEF messages with an NFC reader device 702 including a PHDC manager 708 according to embodiments of the invention.

An NFC Forum tag operations layer 710 is implemented in the NFC reader device 702 below the PHDC Manager layer 708, which exchanges data in tag frames with a tag platform 712 implemented in the NFC tag device 704 below the PHDC agent 706.

According to the invention, the test for new data is facilitated by using a numbering scheme encoded in the identifier field of the NDEF record that encapsulates the IEEE 11073-20601 APDUs.

The invention claimed is:

1. A near field communication reader device comprising:
a transmitter to transmit a request message to a near field communication tag device, the request message being formed according to a predetermined format, the request message including an identifier section in which an identifier that identifies the request message is disposed;
a receiver to receive a response message from the near field communication tag device, the response message being formed based on the request message according to the predetermined format, and the response message including an identifier section in which an identifier that identifies the response message is disposed; and
a processor to generate the identifier that identifies request message, compare the identifier that identifies the request message with the identifier that identifies the response message, wait until a response message is received that has an identifier that is different from the identifier that identifies the request message in order to identify the response message that has the identifier that is different from the identifier of the request message as valid,
wherein the processor generates identifiers of request messages as arithmetic sums of a same constant value and identifiers of received response messages.

2. The near field communication reader device according to claim 1, wherein the processor is further configured to store payload data in a payload section thereof according to the predetermined format.

3. The near field communication reader device according to claim 1, wherein the same constant value is one.

4. The near field communication reader device according to claim 1, wherein the same constant value is two.

5. A near field communication tag device comprising:
a tag receiver to receive a request message from a near field communication reader device, the request message being formed according to a predetermined format, the request message including an identifier section in which an identifier that identifies the request message is disposed;
a tag transmitter to transmit a response message to the near field communication reader device, the response message being formed based on the request message according to the predetermined format, the response message including an identifier section in which an identifier that identifies the response message is disposed; and
a tag processor to read the request message from the tag receiver, to generate a response message and to forward the response message to the tag transmitter, wherein the identifier that identifies the response message is different from the identifier that identifies the request message, only response messages having identifiers different from the identifier that identifies the request message being accepted as valid and acted upon,
wherein the tag processor generates identifiers of response messages as arithmetic sums of a same constant value and identifiers of received request messages.

6. The near field communication tag device according to claim 5, wherein the tag processor is further configured to generate payload data in a payload section according to the predetermined format.

7. The near field communication tag device according to claim 5, wherein the same constant value is one.

8. The near field communication tag device according to claim 5, wherein the same constant value is two.

9. The near field communication tag device according to claim 5, wherein the near field communication tag device is included in a near field communication system that further includes a near field communication reader device, the near field communication reader device including:
a transmitter to transmit a request message to the near field communication tag device, the request message being formed according to a predetermined format, the request message including an identifier section in which an identifier that identifies the request message is disposed;
a receiver to receive a response message from the near field communication tag device, the response message being formed based on the request message according to the predetermined format, and the response message including an identifier section in which an identifier that identifies the response message is disposed; and
a processor to generate the identifier that identifies the request message, to compare the identifier that identifies the request message with the identifier that identifies the response message and to wait until a response message is received that has an identifier is different from the identifier that identifies the request message in order to identify the response message that has the identifier that is different from the identifier of the request message as valid.

10. A near field communication method comprising:
transmitting a request message from a near field communication reader device to a near field communication tag device, the request message being formed according to a predetermined format, the request message including an identifier section in which an identifier of the request message is disposed;
generating a response message in response to the request message, the response message being formed based on the request message according to the predetermined format, the response message including an identifier section in which an identifier that identifies the response message is disposed, the identifier of the response message being different from the identifier of the request message, only response messages having identifiers different from the identifier that identifies the request message being accepted as valid and acted upon; and
transmitting the response message from the near field communication tag device to the near field communication reader device,
wherein identifiers of request messages are generated as arithmetic sums of a same constant value and identifiers of received response messages.

11. The near field communication method according to claim 10, further comprising:
comparing the identifier of the response message with the identifier of the request message; and
accepting the response message as a valid response message if the identifier of the response message is different from the identifier of the request message.

12. The near field communication method according to claim 10, wherein the same constant number is one.

13. The near field communication method according to claim 10, wherein the identifier of the request message is generated by adding the same constant value to an identifier of a last received response message; and
wherein the identifier of the response message is generated by adding the same constant value to an identifier of a last received request message.

14. The near field communication method according to claim 10, further comprising:
  listening to response messages from the near field communication tag device until a valid response message is received.

15. The near field communication reader device according to claim 1, wherein the processor is further configured to determine that the response message is a valid response message when the identifier that identifies the response message is different from the identifier that identifies the request message, and the response message is received within a predetermined time period relative to the request message.

* * * * *